United States Patent
Shimmick et al.

(10) Patent No.: US 6,406,473 B1
(45) Date of Patent: Jun. 18, 2002

(54) PATIENT FIXATION SYSTEM AND METHOD FOR LASER EYE SURGERY

(75) Inventors: John K. Shimmick; Vladimir Lemberg, both of Belmont; Terrance N. Clapham, Jamestown; Charles R. Munnerlyn, San Jose, all of CA (US)

(73) Assignee: VISX, Incorporated, Santa Clara, CA (US)

( * ) Notice: Subject to any disclaimer, the term of this patent is extended or adjusted under 35 U.S.C. 154(b) by 0 days.

(21) Appl. No.: 09/411,785

(22) Filed: Oct. 1, 1999

(51) Int. Cl.⁷ .............................................. A61B 18/18
(52) U.S. Cl. .............................. 606/5; 606/4; 128/898; 351/212
(58) Field of Search .......................... 606/4–6, 10, 13, 606/116; 128/898; 351/211, 212; 604/294

(56) References Cited

U.S. PATENT DOCUMENTS

| | | | | |
|---|---|---|---|---|
| 4,544,246 A | * | 10/1985 | Crane et al. ................. | 351/211 |
| 4,579,430 A | * | 4/1986 | Bille et al. ................... | 351/206 |
| 4,848,340 A | * | 7/1989 | Bille et al. ................ | 128/303.1 |
| 5,258,787 A | * | 11/1993 | Ito et al. ....................... | 351/214 |
| 5,336,215 A | * | 8/1994 | Hsueh et al. .................... | 606/4 |
| 5,350,374 A | * | 9/1994 | Smith ............................. | 606/5 |
| 5,355,895 A | * | 10/1994 | Hay ............................. | 128/745 |
| 5,425,727 A | * | 6/1995 | Koziol ........................... | 606/5 |
| 5,474,548 A | * | 12/1995 | Knopp et al. ................... | 606/4 |
| 5,549,597 A | * | 8/1996 | Shimmick et al. ............. | 606/5 |
| 5,993,438 A | * | 11/1999 | Juhasz et al. .................. | 606/5 |
| 6,004,313 A | * | 12/1999 | Shimmick et al. ............. | 606/5 |
| 6,203,539 B1 | * | 3/2001 | Shimmick et al. ............. | 606/5 |

* cited by examiner

*Primary Examiner*—Linda C. M. Dvorak
*Assistant Examiner*—Ahmed Farah
(74) *Attorney, Agent, or Firm*—Townsend and Townsend and Crew LLP

(57) ABSTRACT

A visual fixation system which enhances the alignment between the eye and a laser beam of a laser eye surgery system, the fixation system often having an adjustable optical train. The optical train of the fixation system allows an eye having a significant refractive error to be accurately focused at a fixation target. To accommodate the refractive error, the adjustable optical train will often project an image of the target so that the projected image is in focus in front of or behind the plane of the patient's eye. The proper projection distance is calculated to accommodate the refractive error of the eye, the calculation preferably based at least in-part on the eye glass prescription for that eye.

11 Claims, 8 Drawing Sheets

PATIENT FIXATION SYSTEM AND METHOD FOR LASER EYE SURGERY

BACKGROUND OF THE INVENTION

1. Field of the Invention

The present invention is generally related to laser eye surgery systems, devices, and methods. In particular, the present invention provides an adjustable focus patient fixation system which can accommodate refractive errors in a patient's eye, presenting a target which appears to the eye to be in focus, and thereby enhancing the patient's ability to stabilize the eye by viewing the target. In some embodiments, the present invention allows patients to maintain accurate focus and enhanced stabilization on a viewing target during changes in the refractive characteristics of the eye by coordinating focus adjustments of the target system with a photorefractive therapy. Hence, the present invention is particularly useful for enhancing the accuracy and efficacy of laser eye surgical procedures such as photorefractive keratectomy (PRK), phototherapeutic keratectomy (PTK), laser in situ keratomileusis (LASIK), and the like.

Selective photoablation of corneal tissues benefits from precise alignment between the eye and a therapeutic laser beam. Known laser eye procedures generally employ an ultraviolet or infrared laser to remove a microscopic layer of stromal tissue from the cornea of the eye to alter its refractive power. The laser removes a selected portion of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. These laser eye surgery systems are adapted for use while the patient is awake. The position of the patient's head will often be stabilized using a headrest pillow, a chin rest, a bite bar, or the like. The patient can further enhance alignment between the eye and the therapeutic laser beam by focussing on a target during the procedure.

Known visual fixation targets typically include a light emitting diode (LED) which is optically positioned about ¼ meter in front of the patient. Unfortunately, patients do not wear corrective lenses during photorefractive surgery. As a result, the target may be blurred or out of focus for many patients. Even more problematic, the optical characteristics of the patient's eye may change significantly during laser eye surgery. As a result, the patient's ability to hold her eye steady by viewing the target can be compromised. In fact, patients have reported losing site of the blurry targets during laser eye surgery. This may cause the patient to look away from the target, degrading alignment between the laser eye system and the eye, and thereby decreasing the accuracy and efficacy of the refractive therapy.

In light of the above, it would be desirable to provide improved ophthalmological systems, devices, and methods. It would be particularly desirable to provide enhanced techniques for stabilizing an eye having a significant refractive error throughout a laser eye surgery procedure. It would further be desirable to provide enhanced methods and devices for initially establishing and maintaining alignment with a patient fixation system to provide enhanced eye stabilization before and during laser eye surgery and other therapeutic or diagnostic procedures for the eye.

2. Description of the Background Art

U.S. Pat. No. 4,478,499, describes an operation microscope which incorporates an eye fixation device. U.S. Pat. No. 5,549,597, describes an in situ axis alignment module for determining the astigmatic axis of a patient, and for aligning the cylindrical axis of a laser ablation system for ophthalmological surgery.

U.S. Pat. No. 5,258,787, describes an ophthalmologic apparatus having an illumination optical system for directing light onto a prescribed point of an eye, and an observation optical system for observing an image of the prescribed point. U.S. Pat. No. 5,557,352, describes a method and apparatus for measuring the visual acuity and refraction of the human eye during and immediately after ocular surgery.

SUMMARY OF THE INVENTION

The present invention generally provides improved laser eye surgery devices, systems, and methods. The invention generally enhances the alignment between the eye and a laser beam of a laser eye surgery system using a visual fixation system having an optical train. The optical train of the fixation system allows an eye having a significant refractive error to be accurately focused at a fixation target. To accommodate the refractive error, the optical train will often project an image of the target so that the image is selectively focussed in front of, at, or behind the plane of the patient's eye. The present invention also encompasses the calculation of the proper projection distance to accommodate the refractive error of the eye, the calculation preferably based at least in-part on the eye glass prescription for that eye.

A particular advantage of the present invention is that it allows the patient to focus upon (and minimize misalignment with) the target system while the eye undergoes significant refractive changes. For example, a patient undergoing a photorefractive therapy for 4.0 D hyperopia will have a significant change in the refractive configuration of the eye during the therapy. To maintain alignment between the changing eye and the laser beam, the present invention encompasses dynamically varying the image plane of the projected target image. Initially, the target image will be projected posterior to the plane of the hyperopic eye. Gradually, as the refractive configuration of the eye is corrected, the projected target image can be moved away from the, plane of the patient's eye. Ideally, a computer controller dynamically varies the position of the projected target image in coordination with the photorefractive therapy. Where the photorefractive therapy proceeds in incremental steps, the adjustable optical train of the fixation system may also be incrementally adjusted, for example, by rotating a turret to select an alternative lens of the optical train. As the adjustable optical train helps the patient focus on the fixation target, the invention greatly enhances the patient's ability to stabilize the eye as it undergoes these changes, and thereby enhances the accuracy and efficacy of the laser resculpting process.

In a first aspect, the present invention provides a laser eye surgery method. The method comprises projecting a target at a first distance from the eye. This projection allows the target to appear in focus to the eye. The eye is stabilized by viewing the target through a cornea of the eye. Refraction of the stabilized eye is altered by selectively removing a portion of the cornea. The target is projected toward the altered eye at a second distance from the eye so that the target appears in focus to the altered eye.

In many embodiments, a target optical train will be adjusted to move a projected image of the target from the first distance to the second distance. For example, when the refractive therapy comprises a treatment for hyperopia, the image can initially be disposed posterior of the cornea. In contrast, when the refraction is altered so as to decrease myopia, the image will first be disposed anterior of the cornea. The image will typically move farther from the eye as the refractive error is corrected. For example, during laser in situ keratomileusis (LASIK), the distance between the projected image and the plane of the eye increases during the therapy.

In other embodiments, particularly where the refraction altering step is performed as a series of incremental improvements to a refractive error of the eye, the target image will be adjusted in a series of corresponding incremental changes. Alternatively, an appropriately designed Fresnel zone plate can simultaneously produce multiple target images in front of and/or behind the patient's eye. Another approach would be to use a holographic optical element such as an appropriately designed diffractive optic hologram or Fresnel zone plate to project a pre-selected target shape at multiple desired positions in front of and/or behind the eye. The projected target shapes may have differing colors (or the like) at differing positions. Alternatively, a continuum of target images might be projected so as to define a line along the optical axis of the eye. The patient will then see the target image at the portion of the line corresponding to the proper separation distance between the eye and the target image location.

Preferably, the first distance will be calculated based at least in-part on an eye glass prescription of the eye. At least one intermediate distance may also be calculated based on an intermediate refractive configuration of the eye. This intermediate configuration may be either measured or estimated based on the known photoablative effects of a laser beam during photorefractive therapy, for example. A processor may simultaneously adjust the optical train and control photoablative sculpting of the cornea so that the target remains substantially in focus to the eye throughout the procedure.

In another aspect, the present invention provides a method comprising projecting a target toward an eye having a refractive error. The target is projected so that a focused image of the target is separated from the eye by a pre-calculated separation distance, and so that the target appears to be in focus to the eye. The eye is stabilized by viewing the projected target through a cornea of the eye.

In another aspect, the present invention provides a laser eye surgery system for resculpting a cornea of a patient's eye. The laser system comprises a laser to produce a laser beam for photoablating a portion of the cornea. Delivery optics are optically coupled to the laser so as to effect a predetermined change in refraction of the cornea with the laser beam. A target optical train is aligned with the delivery optics to help the patient stabilize the eye. The optical train is capable of projecting the target toward the eye at a plurality of separation distances from the eye. This allows the system to accommodate a plurality of corneal refractive configurations of the eye.

Preferably, a computer controller couples the laser system delivery optics to the target optical train so that the optical train moves an image of the target in coordination with changes in the cornea. This allows the image to appear in focus to the eye despite the refractive changes taking place. The movement of the image may be smooth and gradual, or may be incremental. Preferably, at least a portion of the delivery optics and target fixation system are coaxially aligned. In some embodiments, the optical train may project the image simultaneously at a plurality of distances, typically using a holographic optical element, a Fresnel zone plate, or the like. It is generally preferable to project the target towards the eye so that the target appears within an angular sub-tense of less than about 80 mins. of arc at a pupil of the eye.

In yet another aspect, the present invention provides a laser eye surgery system for correcting refractive errors of an eye. The laser system comprises a laser to produce a laser beam for selectively removing a portion of a cornea of the eye. Delivery optics in an optical path of the laser beam transmit the laser beam toward the cornea so as to alter the eye from a first refractive configuration to a second refractive configuration. The target fixation system includes a target and target optics. The target optics are aligned with the optical path to help maintain alignment between the eye and the laser beam. The target optics project the target at a first distance and at a second distance. The target appears in focus to the eye when the cornea is in the first configuration and the target is projected at the first distance. The target also appears in focus to the eye when the cornea is in the second configuration and the target is projected at the second distance.

DESCRIPTION OF THE SPECIFIC EMBODIMENTS

The present invention is generally directed to structures, systems, and methods for measuring and/or treating a human eye. The techniques of the present invention generally enhance alignment between the eye and a treatment or measurement device. Known ophthalmological devices often include structures that support the patient's head, such as a pillow, a chin rest, a bite bar, or the like. The invention presents a viewing target to the eye which appears in focus to the patient despite an often significant refractive error of the patient's eye, significantly enhancing the patient's ability to stabilize viewing with the focused target. Hence, the systems, devices, and methods of the present invention will find use with devices such as corneal topography machines, auto-refractors, and particularly, laser eye surgery systems.

The techniques of the present invention are particularly well adapted for use during procedures which will significantly alter the refractive configuration of the eye. Maintaining proper alignment between the eye and such interventional devices can greatly enhance the efficacy of a therapeutic procedure. For example, photoablative resculpting of the cornea to correct a refractive error significantly benefits from accurate alignment between the resculpting laser beam and the eye. The resculpting process takes a significant amount of time to change the refractive configuration of the eye. By increasing the patient's ability to focus on the target of the visual fixation system, the accuracy and efficacy of the resculpting process is improved. Hence, while the visual fixation system of the present invention may find applications in a wide variety of ocular measurements and therapies, the most immediate application will be in the field of laser eye surgery so as to enhance the benefits of photorefractive keratectomy (PRK, including procedures to correct hyperopia, myopia, astigmatism, or any combination thereof), phototherapeutic keratectomy (PTK), laser in situ keratomileusis (LASIK), and the like.

Figure 1:
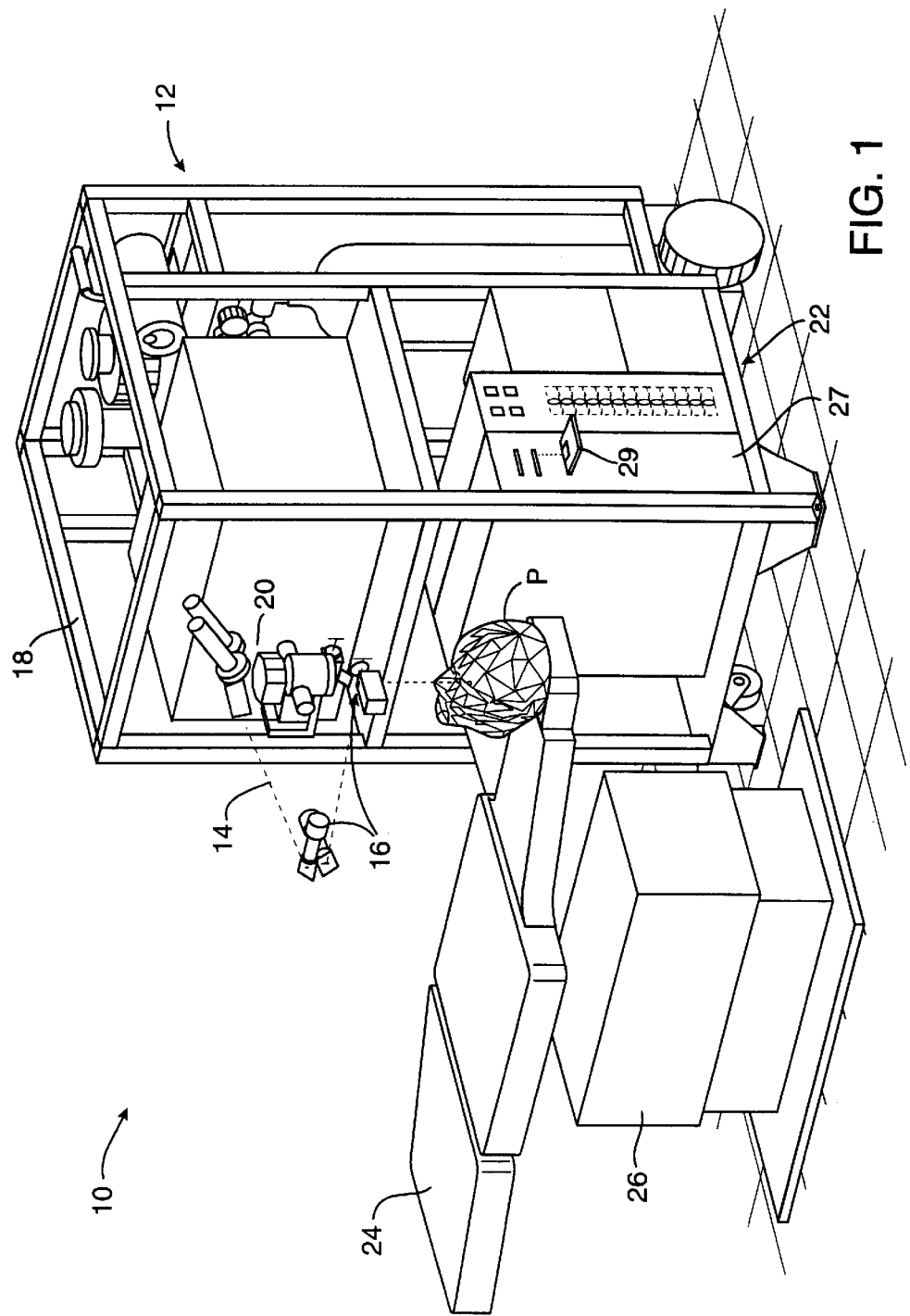
FIG. 1 is a perspective view of a laser eye surgery system according to the principles of the present invention.

Referring now to FIG. 1, a laser eye surgery system 10 includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure.

Laser 12 generally comprises an excimer laser, ideally comprising an argon-florine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye.

Laser 12 and delivery optics 16 will generally direct laser beam 14 to the eye of patient P under the direction of a computer 22. Computer 22 will generally selectively adjust laser beam 14 to expose portions of the cornea to the pulses of laser energy so as to effect a predetermined resculpting of the cornea and alter the refractive characteristics of the eye.

Laser beam 14 may be adjusted to produce the desired resculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997, the full disclosures of which are incorporated herein by reference. Still further alternatives are possible, including scanning of the laser beam over the surface of the eye and controlling the number of pulses and/or dwell time at each location, as described, for example, by U.S. Pat. No. 4,665,913 (the full disclosure of which is incorporated herein by reference); using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); or the like. The computer programs and control methodology for these laser tailoring techniques are well described in the patent literature.

Additional components and subsystems will generally be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

The head of patient P will be firmly supported by, and preferably restrained upon, a patient chair 24. Positioning of the eye relative to the laser delivery optics is generally effected by movement of patient chair 24. Hence, patient chair 24 is supported by an actuation mechanism 26 which can move the patient in three dimensions to axially and laterally position the cornea of the eye at a predetermined target treatment site. Alternatively, at least a portion of the laser delivery optics may move to align laser beam 14 with the cornea.

Laser system 10 will generally include a programmable controller 27. Controller 27 may comprise (or interface with) a conventional PC system including the standard user interface devices such as a keyboard, a display monitor, and the like. Controller 27 will typically include an input device such as a magnetic or optical disk drive, an internet connection, or the like. Such input devices will often be used to download a computer executable code from a tangible storage media 29 embodying the methods of the present invention. Tangible storage media 29 may take the form of a floppy disk, an optical disk, a data tape, or the like, and the controller 27 will include the memory boards and other standard components of modern computer systems for storing and executing this code.

Figure 2:
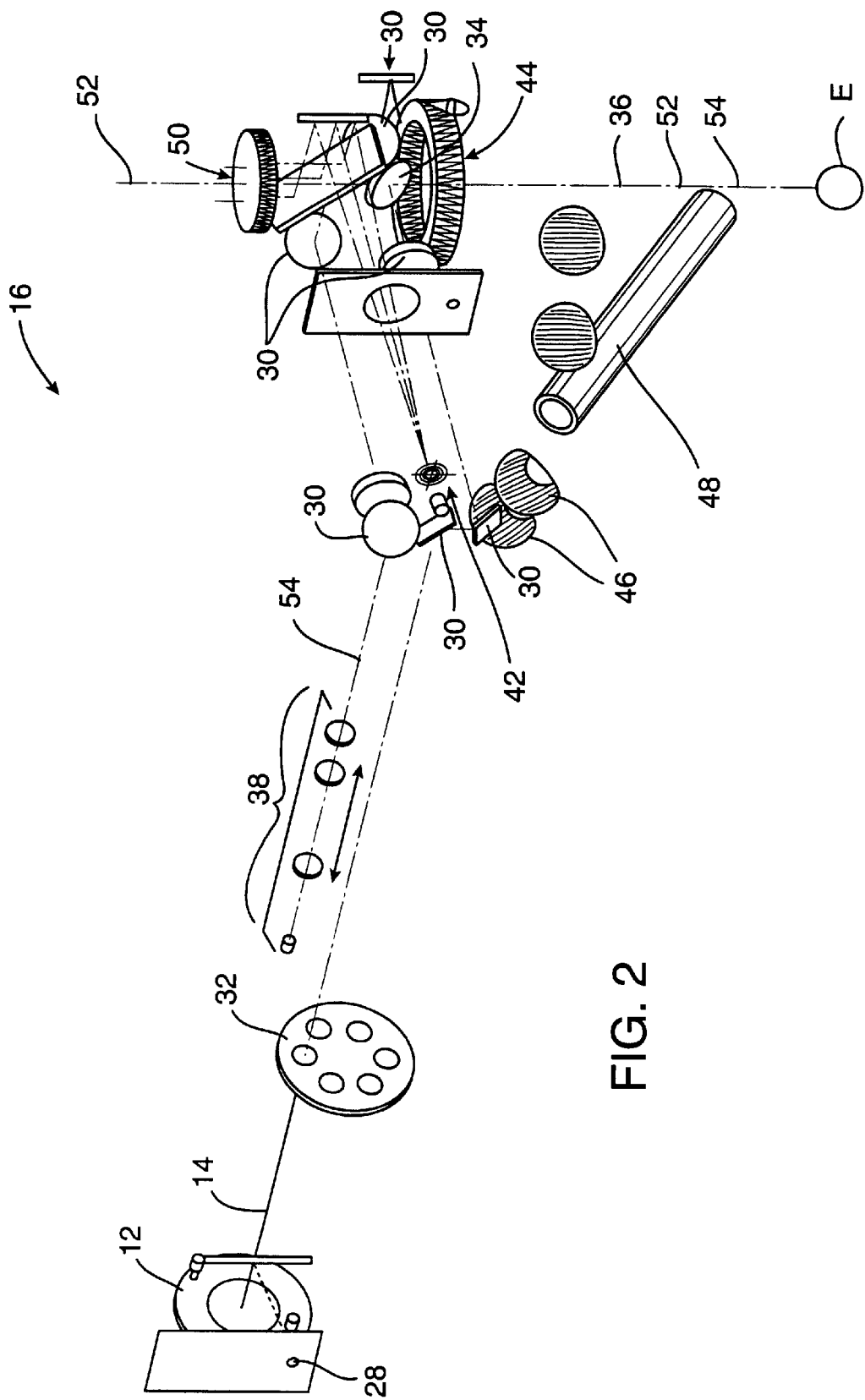
FIG. 2 is a perspective view of some of the optical components of a laser eye surgery system similar to that of FIG. 1, including an adjustable target fixation system.

Referring now to FIG. 2, several of the components of delivery optics 16 are illustrated with adjacent subsystems of the laser system. After passing a laser energy detector 28, laser beam 14 from laser 12 is directed through an aperture wheel 32. The laser beam then continues to a beam splitter 34 which directs laser beam 14 along a treatment axis 36 to eye E.

Of particular importance to the present invention, an adjustable focus patient fixation system 38 helps the patient maintain eye E in the proper orientation, as will be described in detail herein below. A patient positioning system will often help the laser system operator properly position the patient for treatment. A virtual reticle projection system 42 can project a reticle into the microscope, as shown. Illumination of the eye can be provided using a ring illuminator 44 and oblique illuminators 46, while aspiration nozzle 48 aspirates photodecomposition debris. In the exemplary embodiment, objective lens 50 of microscope 20 (see FIG. 1) is tightly structurally coupled to the downstream elements of laser delivery optics 16. An axis 52 of microscope 20, a projection axis 54 of patient fixation system 38, and treatment axis 36 of laser beam 14 are coaxially aligned adjacent eye E.

Figure 3:
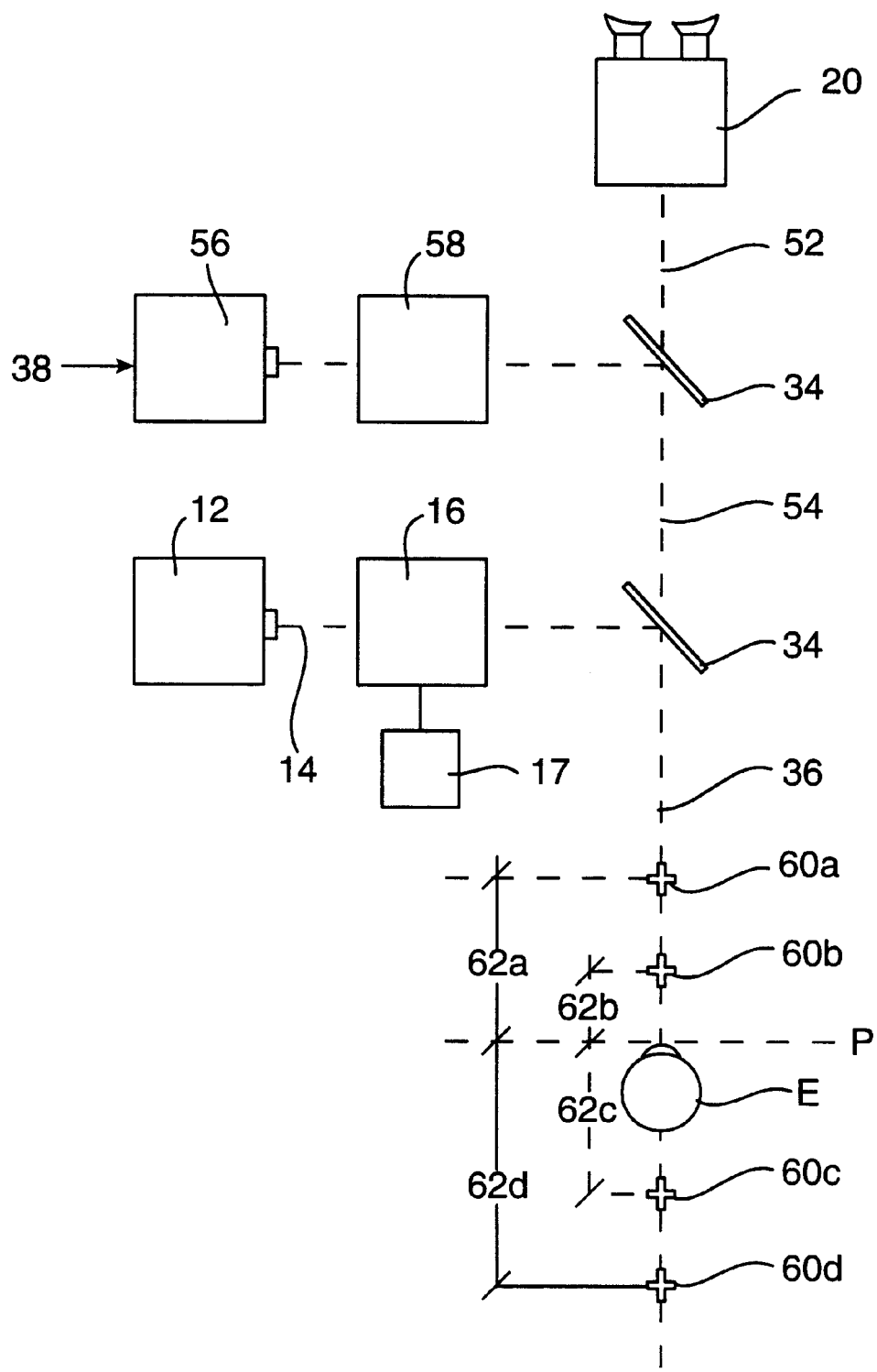
FIG. 3 is a schematic illustration of the laser eye surgery system of FIG. 1, illustrating a method for its use.

The alignment of microscope 20, patient fixation system 38, and laser beam 14 is schematically illustrated in FIG. 3. In general, patient fixation system 38 includes a light source 56 and a target optical train 58. Optical train 58 is capable of projecting targets 60a, b, . . . at a plurality of distances. More specifically, optical train 58 can image targets 60 at a plurality of separation distances 62a, b, . . . from a plane P of eye E. The optical train often (though not always) will be adjusted using an adjustment mechanism to vary the separation distance.

For a given refraction of eye E, a projected image will generally only be in focus over a limited range of separation distances from the eye. Where eye E has little or no refractive error, target 60 will appear in focus to the eye when optical train 58 projects the target image very far from plane P of the eye, so that the separation distance is at least one meter. Patients having myopia will generally perceive target 60 as being in focus when optical train 58 projects the target image anterior to plane P of eye E, such as at separation distances 62a, or 62b. The greater the myopia the shorter the separation distance should be: to accommodate a significant amount of myopia, target 60b is projected at a significantly shorter separation distance 62b in front of eye E relative to the longer separation distance 62a used to adjust for a more moderate myopia of eye E. Similarly, varying degrees of hyperopia can be accommodated by projecting target 60c, 60d, posterior to plane P by varying separation distances 62c, 62d.

The benefits and challenges of maintaining alignment with eye E are particularly significant during laser eye surgery. During laser eye surgery (and some other procedures), bright lights are directed toward the eye along with the fixation target (for example, from ring illuminator 44 and/or oblique illuminators 46 as shown in FIG. 2). These lights will reduce the contrast of the target image seen by the patient, and may degrade the quality of the target image as it is viewed. Unfortunately, these bright lights are beneficial for other aspects of the laser procedure, such as for enhancing the image of the eye provided by an operating microscope.

The corneal surface is often dry during laser eye surgery. In fact, an epithelial layer will often be removed from the cornea before resculpting begins using a laser, a brush or a scraping tool, which may leave the cornea roughened. A dry, roughened cornea will scatter light from the patient fixation system and other illumination sources, further reducing image contrast. Where the contrast of the target image is compromised, and where the target is out of focus (due to a refractive error of the eye, temporary and/or permanent changes to the eye during the procedure, or the like) the patient may be unable to see the target, and alignment between the eye and the laser may be lost.

Loss of alignment between eye E and laser beam 14 may have a number of negative implications. Laser eye systems which track the eye and terminate therapy upon loss of alignment may temporarily or permanently halt the ablation so that therapy is delayed or incomplete. If therapy proceeds despite the misalignment, the laser resculpting process may produce an uncentered ablation, and could induce astigmatism in the eye.

Figure 4A:
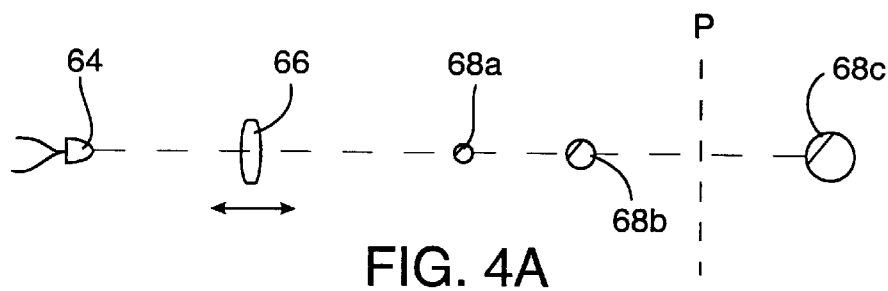
FIGS. 4A–4E schematically illustrate adjustable optical trains for varying a projection distance of an image of a target so as to accommodate refractive errors of an eye before and/or during an optical measurement or therapeutic procedure.
Figure 4B:
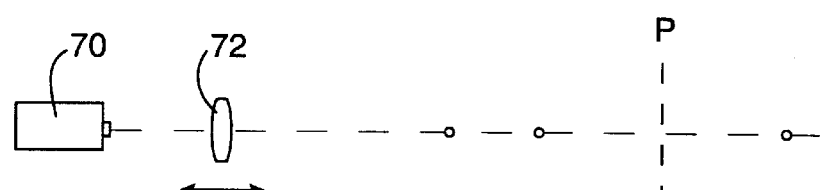

To help the patient establish and maintain the desired orientation of eye E, visual fixation system 38 may include any of a variety of alternative adjustable optical trains as illustrated in FIGS. 4A–E. In the embodiment of FIG. 4A, a light emitting diode (LED) 64 projects light through a moveable lens 66 so as to project an image of a target 68 at varying separation distances from plane P. The location of target image 68 can be varied by axially translating lens 66. Similar variation in the separation distance may be provided without substantially varying the size of the target by axially translating a lens 72 relative to a laser diode 70 where the lens is optically coupled to the laser diode, as illustrated in FIG. 4B.

The adjustable optical train will preferably be under computer control and synchronized with the laser sculpting process. As the laser ablates the cornea and alters the refractive configuration of the eye, the adjustable optical train varies the separation distance under the dynamic control of the computer so that the image of the target, as viewed by the patient, remains substantially in focus. The laser resculpting process will typically take between about 10.0 secs. and 3.0 mins. to complete, and the delivery optics of the laser surgery system will also often be computer controlled. Adjustment of the adjustable optical train may be based on real time topographical measurements of the cornea during the photoablation process. Alternatively, the adjustable optical train will be varied by the computer per calculated intermediate configurations of the eye during resculpting.

Figure 4C:
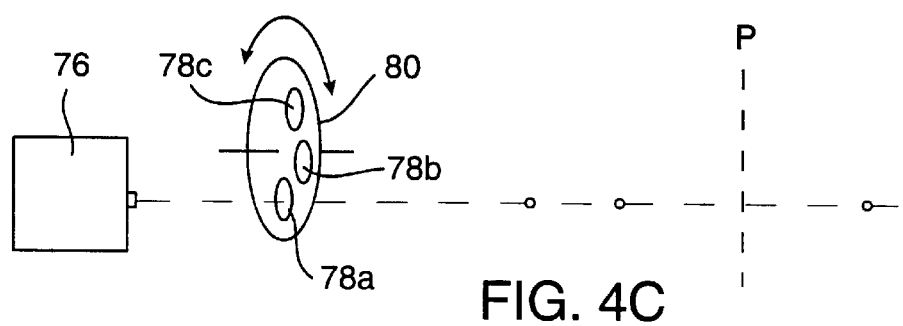

As an alternative to the gradually adjustable target optical trains of FIGS. 4A and B, the visual fixation system of FIG. 4C allows incrementally adjustments of the separation distance. A light source 76 transmits light which passes through a first lens 78a mounted on a rotatable turret 80. Rotating the turret as indicated selects alternative lenses 78b, 78c . . . , thereby incrementally varying the separation distance of the optical train. The focal lengths of the alternative lenses are selected so as to project light to a small spot at a desired separation distance relative to the corneal plane P of the eye.

Figure 4D:
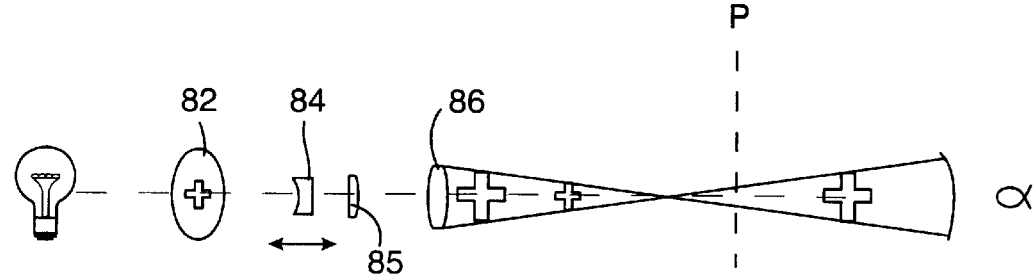

Referring now to FIG. 4D, adding more lenses to the above optical trains may provide still further advantages. For example, it is often desirable to keep the angular sub-tense of the target features within 80 mins. of arc at the patient's pupil. In the visual fixation system of FIG. 4D, an aperture 82 allows the system to project a target having a desired shape, such as a cross, a circle, or a reticle. The optical train has a translatable plane concave lens 84 with a focal length of −25 mm, and a neighboring plane convex lens 85 with a focal length of 50 mm. The optical train further includes a biconvex lens 86 having a focal length of 150 mm positioned 300 mm from the corneal plane of patient's eye P. By translating lens 84, the projected target image may be properly positioned for patients having refractive errors from +5 to −15 D. For an aperture with a physical size of 1.0 mm, this optical system can limit the site of the images aperture to within 15 mins. of arc over the entire +5 to −15 D range.

Figure 4E:
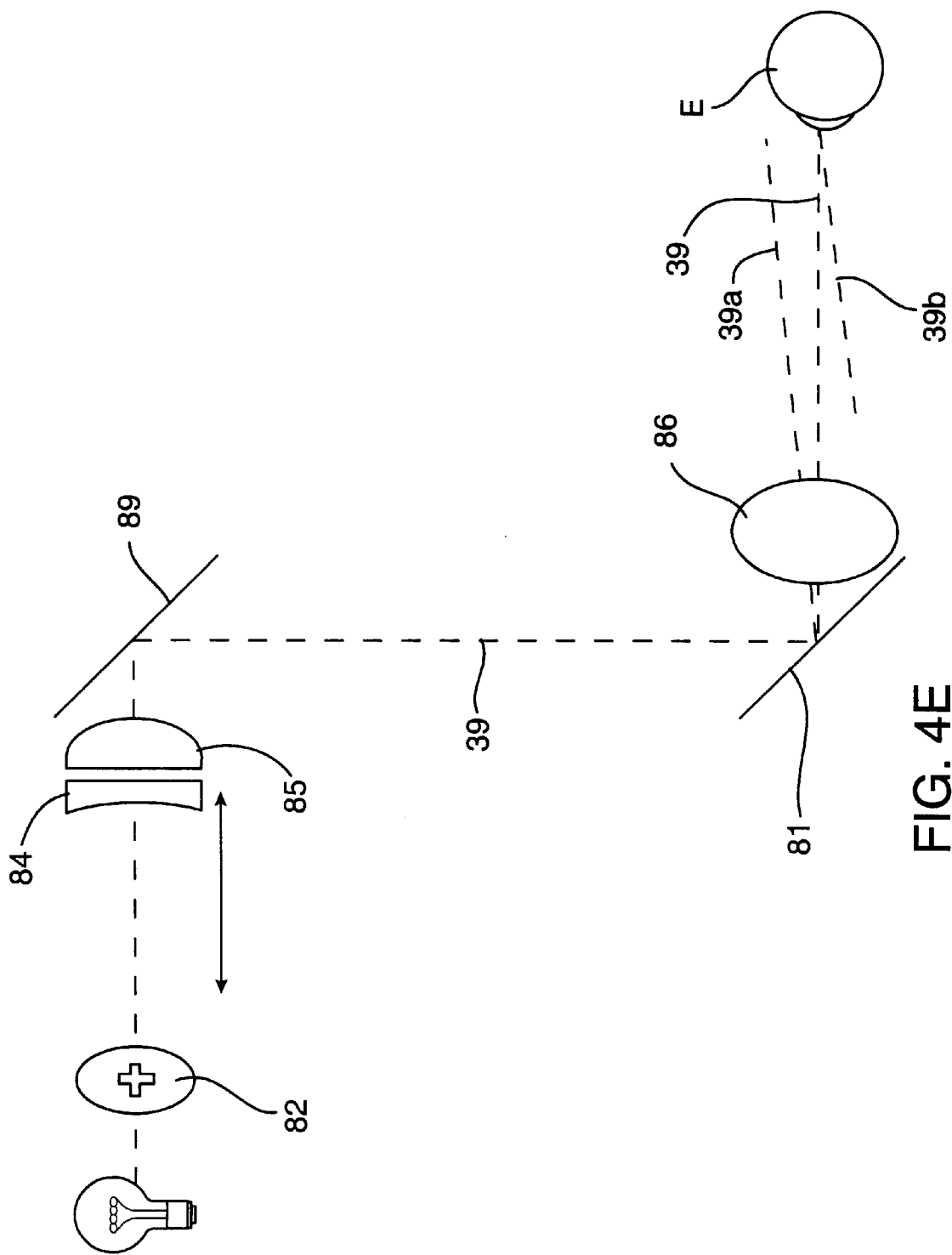

The preferred embodiment of the optical train includes the optical elements shown in FIG. 4E. Lens 86 has a 150 mm focal length and is positioned 300 mm from the eye. Lens 85 has a 50 mm focal length and is 325 mm from lens 86 and 135 mm from target 82. Lens 84 has a −25 mm focal length and can be slid about 100 mm from lens 85 toward target 82 to present a focused target for corneal plane refractions from +5 to −15 D. With this configuration, a 1 mm target will subtend about 15 mins. of arc at the plane of the patient's pupil.

In an exemplary embodiment, two mirrors are inserted into this optical train to facilitate alignment. A first mirror 81 is positioned adjacent to lens 86. Changes to the angle of mirror 81 will offset target projection axis 39 about the plane of the eye as shown by offset target projection axis 39a.

Therefore, mirror 81 is rotated to make laser treatment axis 36 coaxial with target projection axis 39 at the plane of the eye. A second mirror 89 is positioned about 300 mm from lens 86 and adjacent to lens 85. This second mirror 89 is imaged about the plane of the eye. Therefore, changes in the angle of mirror 89 will not substantially offset target projection axis 39 at the plane of the eye, but will instead primarily change the angle of target projection axis 39 as shown by rotated target projection axis 39*b*. Consequently, second mirror 89 is rotated to keep the images seen by the patient aligned so that the eye will not move when viewing fixation target images at different separation distances as the refraction of the eye changes during surgery.

Figure 5A:
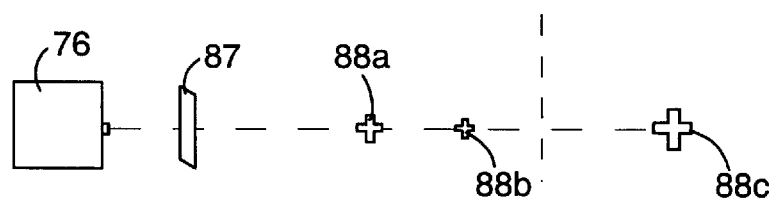
FIGS. 5A–5C schematically illustrate optical trains for simultaneously projecting a target at a plurality of distances from a plane of an eye.

A still further alternative fixation system is schematically illustrated in FIG. 5A. Rather than projecting a single target image at a single adjustable separation distance, the fixation system of FIG. 5A simultaneously projects a plurality of target images 88*a, b, c* . . . The target image which is closest to being at the proper separation distance will be substantially in focus to the patient's eye, while the other target images are blurred.

Figure 5B:
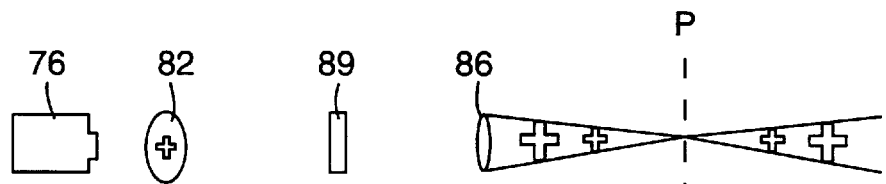

To simultaneously project a target at a plurality of projection distances, light from light source 76 passes through a multiple projection element 87. A variety of optical structures may be used as multiple projection element 87. For example, an appropriately designed Fresnel zone plate will produce multiple diffraction maxima before and/or after the patient's eye. Another approach is to use a holographic optical element (HOE) such as an appropriately designed diffractive optic or hologram to project a pre-selected target shape to desired positions before and/or after the eye. Such multiple projection elements may avoid the need for, or decrease the complexity of, dynamic control systems for the target optical train in laser eye surgery systems. One suitable multiple projection element would be a diffractive optic 89 that produces multiple images of aperture 82 as shown in FIG. 5B. One source for diffractive optic 89 is the Digital Optics Corporation of North Carolina. The diffractive optic 89 is preferably imaged by lens 86 onto plane P with a magnification of 1.0. The appropriate focal lengths of diffractive optic 89 to project multiple images before and after plane P may be readily calculated.

Figure 5C:
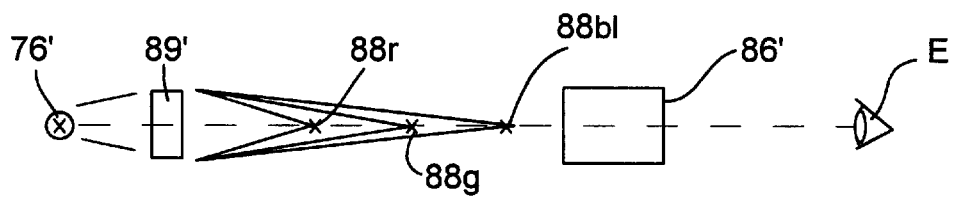

Referring now to FIG. 5C, it is also possible to project visually distinct target images towards the eye. An alternative diffractive optic 89' with negative dispersion images a broadband light source 76' at distances which vary with wavelength. For example, red target 88*r*, green target 88*g*, and blue target 88*bl* images are separated, and can then be transmitted or reimaged toward eye E at the appropriate focal lengths, size, and the like, by reimaging optical system 86'. Such visually distinct (here different color) target images can positively indicate to the patient the progress of a photorefractive procedure, as the color of the target will appear to change in a predictable manner.

Figure 6:
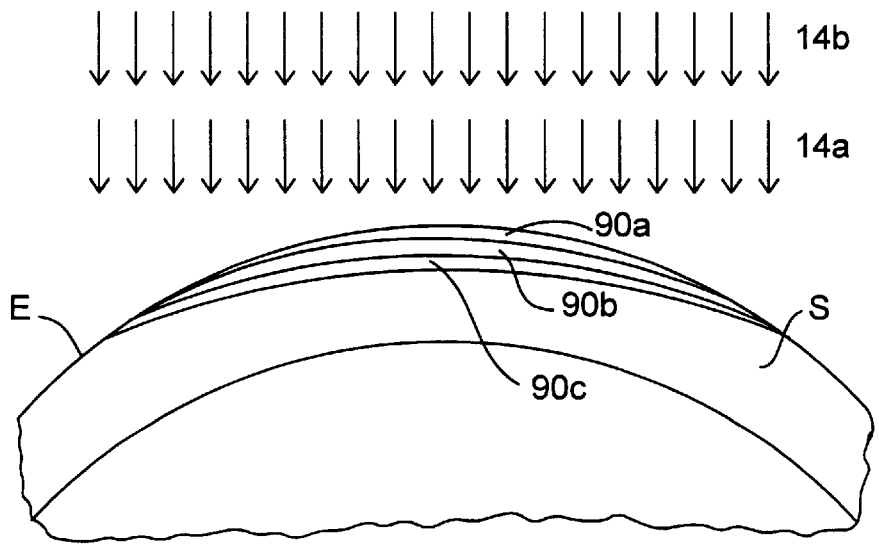
FIG. 6 schematically illustrates a method for incrementally altering a refractive configuration of the eye.

As the laser selectively removes portions of the cornea, aberrations may be temporarily ablated on the eye. To decrease any deleterious effects of the aberrations on the patient's vision (which might temporarily limit the patient's ability to focus on the visual fixation target, and possibly inflicting correctable damage to the eye sight if the ablation process has to be permanently terminated before completion), a refractive treatment may be broken into a series of treatments which incrementally improve a refractive defect of the eye. Even where these sub-treatments are performed immediately following one another, this method of breaking the treatment into a series of smaller corrections will minimize aberrations created during the ablation process. This aspect of the present invention is schematically illustrated in FIG. 6.

A patient with a spherical refractive error of minus ten (−10) diopters can be corrected with a series of two diopter corrective treatments. The imaging system will initially project a target to the separation distance corresponding to the −10.0 D position, that is, for myopia, at a separation distance of 0.1 meters in front of the patient. A first series of laser pulses 14*a* selectively removes a first portion 90*a* of stroma S, thereby effecting a two diopter correction of the patient's myopia. At this point, the target can projected to a separation distance appropriate to −8.0 D of myopia, which would be 0.125 meters in front of the plane of the patient's eye.

Advantageously, after this first portion of the treatment, eye E has the benefit of a partial treatment which improves the refractive error of the eye. This allows the eye to focus accurately at the adjusted target image (or at a different target image where a multiple simultaneous projection fixation system is used), and also results in a net benefit to the eye if the therapy must be terminated at that point. A second series of laser pulses 14*b* can then be directed at the eye while the eye is viewing the adjusted target, so that a second portion of 90*b* of stroma S is removed, once again effecting a two diopter correction. The incremental resculpting process is repeated as sub-treatments until the patient refraction has achieved a desired endpoint. Advantageously, even if the treatment is interrupted during a sub-treatment, for example, where one side of the eye has had a portion of the stroma removed but the other side has not, the resulting aberration or astigmatism of the eye will be limited. This is in contrast to methods in which the laser beam removes the stroma to the final depth along one portion of the eye and then continues the ablation on an alternative portion of the eye, which could result in significant aberrations.

The present invention further encompasses calculation of the separation distance for projection of the visual fixation target image based at least in-part on the eye glass prescription of a patient's eye. As the patient's refraction is typically known prior to laser eye surgery (or other ophthalmological measurements or therapies), the visual fixation system may be preadjusted to project a target which will be substantially in focus to the patient. This increases the efficiency and speed of the measurement or surgical procedure.

Figures 7A, 7B:
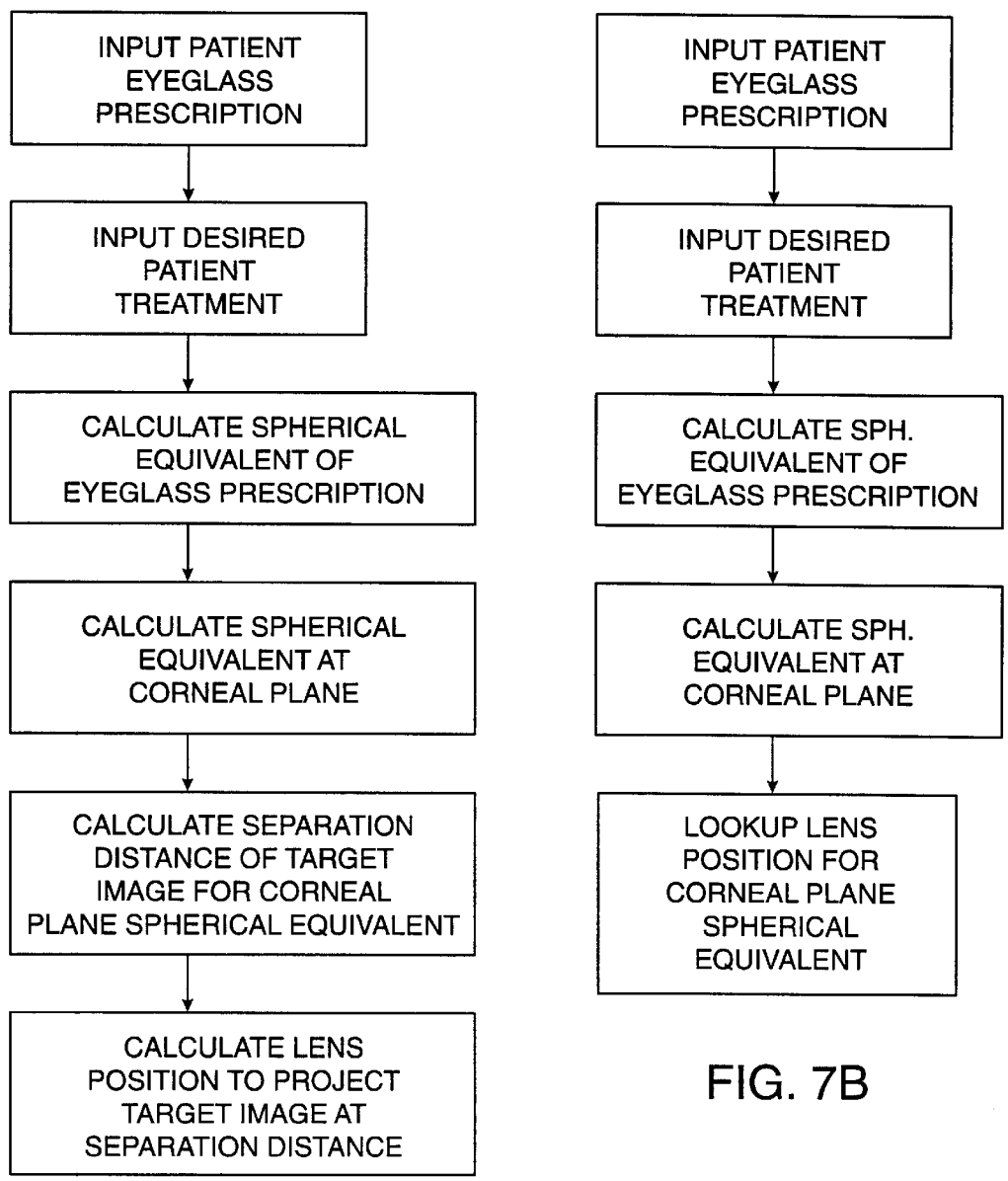
FIGS. 7A and 7B are flow charts of a method to determine target distances and lens positions based on an eyeglass prescription of a patient.

FIG. 7A is a flow chart showing a method for calculating the separation distance. The separation distance between the target image and corneal plane P is initially calculated from the patient's eyeglass prescription. For patients with spherical prescriptions, the target position is calculated using the formula $$S = 1/D$$

where S is the separation distance in meters and where D is the spherical component of the patient eyeglass prescription in diopters. For patients with astigmatism, the spherical equivalent of the eyeglass prescription may be used instead of the spherical component. In a preferred embodiment, the patient prescription at the corneal plane is used to calculate the separation distance, as illustrated in FIG. 7A. The separation distances for corneal plane prescriptions from +5 to −15 D are show in Table 1. This table also shows the separation between plane concave lens 84 and plane convex lens 85 in the embodiment shown in FIG. 4D. Once calculated, the positions may be stored in computer memory and looked up when needed as shown in FIG. 7B. This storing of values expedites the execution of the computer program because the computer does not need to perform as many calculations.

| Lens System Imaging | |
|---|---|
| Prescription (D) | Separation Distance (m) |
| −15 | 0.06666667 |
| −14 | 0.07142857 |
| −13 | 0.07692308 |
| −12 | 0.08333333 |
| −11 | 0.09090909 |
| −10 | 0.1 |
| −9 | 0.11111111 |
| −8 | 0.125 |
| −7 | 0.14285714 |
| −6 | 0.16666667 |
| −5 | 0.2 |
| −4 | 0.25 |
| −3 | 0.33333333 |
| −2 | 0.5 |
| −1 | 1 |
| 0 | |
| 1 | −1 |
| 2 | −0.5 |
| 3 | −0.33333333 |
| 4 | −0.25 |
| 5 | −0.2 |

Figure 8:
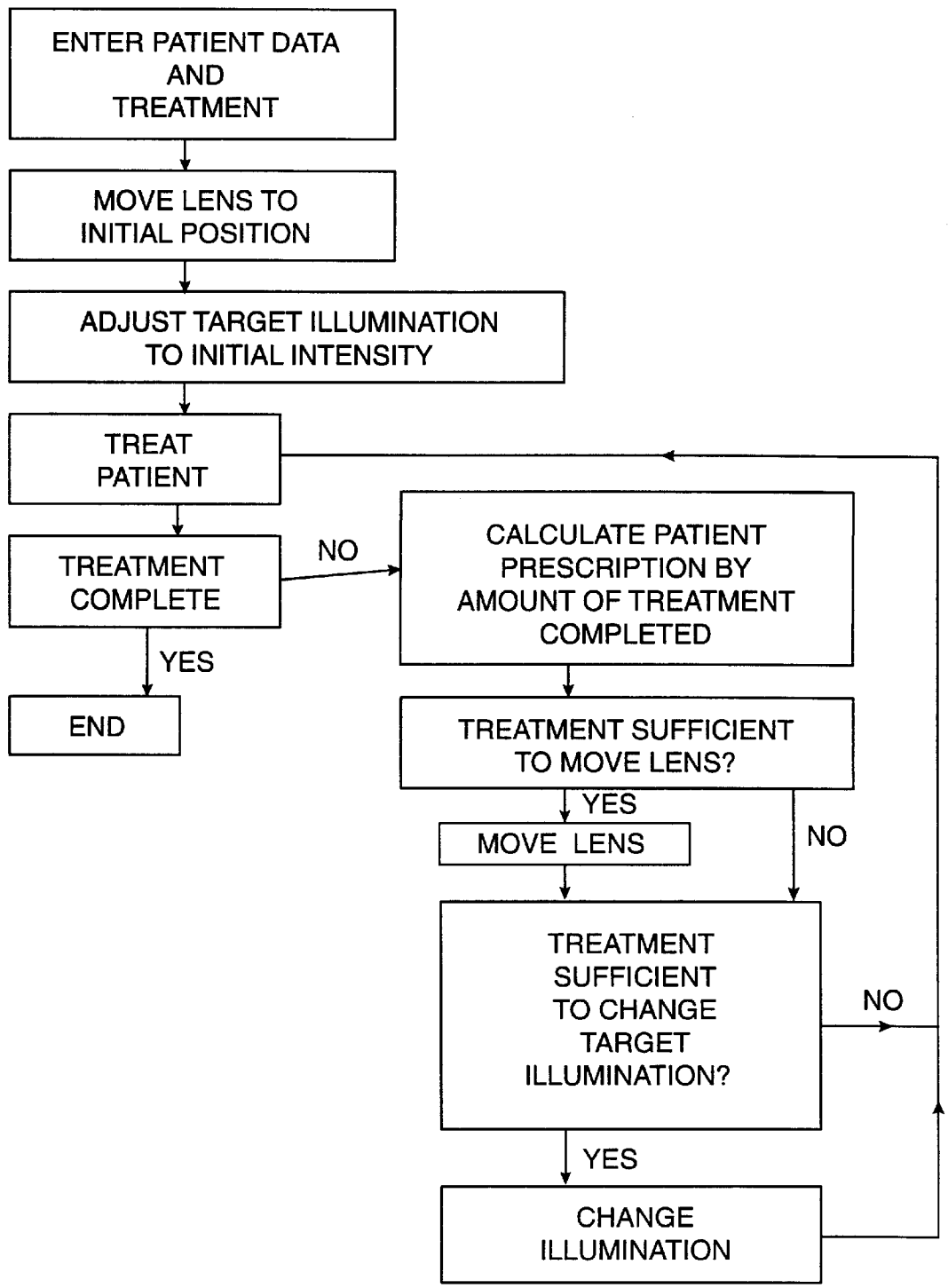
FIG. 8 is a flow chart of a method for controlling and adjusting a fixation target image during a refractive procedure.

During the surgery, the lens position and target illumination intensity may be dynamically controlled as illustrated by the flow chart shown in FIG. 8. The target image is initially positioned according to the patient's eyeglass prescription, and the target illumination intensity is adjusted according to the patient's eyeglass prescription. The intensity adjustment is desirable in embodiments where the intensity of the target image varies with the separation distance. The treatment is initiated and monitored until completion. During the treatment, the patient's intermediate eyeglass prescription is calculated by subtracting the amount of treatment completed from the initial eyeglass prescription. When the calculated eyeglass prescription reaches a predetermined value, the lens is moved to project the target image to a new separation distance corresponding to the calculated eyeglass prescription. Similarly, when the calculated eyeglass prescription reaches a predetermined value, the target illumination intensity is changed to a value related to the calculated patient eyeglass prescription. Because of variability in surgical technique, the target illumination intensity may be initially set by the surgeon, and then varied by the calculated patient eyeglass prescription. When the treatment is completed, the monitoring and associated calculations are stopped.

While the exemplary embodiment has been described in some detail, by way of example and for clarity of understanding, a variety of modifications, changes, and adaptations will be obvious to those of skill in the art. For example, the optical train of the target fixation system may also include a series of alternatively selectable lenses which correct for an astigmatism initially present in or temporarily imposed on the eye during a laser eye surgery. Adjustment of the target fixation system may also compensate for the significant temporary change in refraction when an anterior portion or flap of the cornea is displaced during LASIK procedure. Hence, the scope of the present invention is limited solely by the appended claims.

What is claimed is:

1. A method comprising the steps of:

projecting a target toward an eye having a refractive error so that a focused image of the target is separated from the eye by a calculated separation distance and the target appears in focus to the eye;

stabilizing the eye by viewing the projected target through a cornea of the eye while altering refraction of the eye by selectively removing a portion of the cornea so as to reduce the refractive error; and calculating the separation distance based at least in part on changes to the refractive error imposed during the altering of refraction.

2. The method of claim 1, wherein calculating the separation distance is further based at least in part on an eyeglass prescription of the eye.

3. The method of claim 1, wherein the refractive error comprises myopia or hyperopia.

4. The method of claim 1, further comprising adjusting a target optical train to move the projected image of the target to the calculated separation distance.

5. The method of claim 4, wherein the adjusting is in response to a signal from a controller.

6. A method comprising the steps of:

projecting a plurality of target images toward an eye having a refractive error, wherein each target image is separated from the eye by a different separation distance and at least one target image appears in focus to the eye; and stabilizing the eye by viewing the at least one target image through a cornea of the eye while altering refraction of the eye by selectively removing a portion of the cornea so as to reduce the refractive error.

7. A method as in claim 6, wherein at least two target images vary by size when viewed through the cornea of the eye.

8. A method as in claim 6, wherein at least two target images vary by color when viewed through the cornea of the eye.

9. A method as in claim 6, wherein the plurality of target images are projected simultaneously.

10. A method as in claim 6, wherein the projecting step includes passing light through a multiple projection element to form the plurality of target images.

11. A method as in claim 10, wherein the multiple projection element is selected from the group consisting of Fresnel zone plates, holographic optical elements, diffractive optics, and holograms.

* * * * *